United States Patent [19]

Goring

[11] 4,451,449

[45] May 29, 1984

[54] XANTHINE DERIVATIVES, AND THEIR USE IN PHARMACEUTICAL COMPOSITIONS

[75] Inventor: Joachim E. Goring, Gronau, Fed. Rep. of Germany

[73] Assignee: Johanna Wuelfing, Fed. Rep. of Germany

[21] Appl. No.: 278,569

[22] Filed: Jun. 29, 1981

Related U.S. Application Data

[63] Continuation of Ser. No. 135,284, Mar. 31, 1980, abandoned.

[30] Foreign Application Priority Data

Apr. 5, 1979 [GB] United Kingdom ................. 7912050

[51] Int. Cl.³ .................... C07D 239/95; A61K 31/52
[52] U.S. Cl. ................................... 424/253; 544/267; 544/268

[58] Field of Search ............... 544/268, 269, 267, 271; 424/253

[56] References Cited

U.S. PATENT DOCUMENTS

3,737,433   6/1973   Mohler et al. .................... 544/271

FOREIGN PATENT DOCUMENTS

200367   2/1955   Australia ............................ 424/253

OTHER PUBLICATIONS

CA, vol. 72, 21697j, (1970).
CA, vol. 94, 167711k, (1981).

*Primary Examiner*—Nicholas S. Rizzo
*Attorney, Agent, or Firm*—Jacobs & Jacobs

[57] ABSTRACT

Ketals of 1-(1,3-dialkylxanthin-7-yl)propan-2-ones are of use in the treatment of vascular disorders. A representative embodiment is 2-methyl-2-(1,3-dibutylxanthin-7-ylmethyl)-1,3-dioxalane.

13 Claims, No Drawings

XANTHINE DERIVATIVES, AND THEIR USE IN PHARMACEUTICAL COMPOSITIONS

CROSS-REFERENCE

This is a continuation of Ser. No. 135,284 filed Mar. 31, 1980, and now abandoned.

British Patent Specification No. 1,441,562 discloses inter alia that compounds such as those of the formula (I):

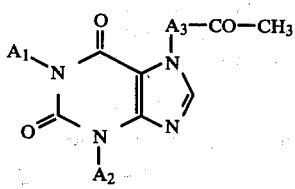

wherein $A_1$ and $A_2$ are alkyl groups and $A_3$ is an alkylene moiety, possess blood flow improving properties. It was said in Specification No. 1,441,562 that the compound of the formula (I) wherein $A_1$ and $A_2$ are n-butyl groups and $A_3$ is a $CH_2CH_2$ group was particularly effective. It has now been found that ketals of the compound of the formula (I) wherein $A_1$ and $A_2$ are n-butyl groups and $A_3$ is a $CH_2CH_2$ group do not possess potent blood flow enhancing properties. It has been found that certain other ketals do possess good blood flow enhancing properties.

The present invention provides the compounds of the formula (II):

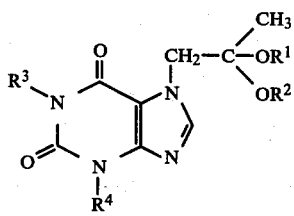

wherein
$R^1$ is a lower alkyl group and $R^2$ is a lower alkyl group; or
$R^1$ and $R^2$ together are ethylene, trimethylene or tetramethylene; and
$R^3$ and $R^4$ are the same or different and are each a lower alkyl group;

When used herein the term "lower" means containing 1 to 4 carbon atoms. Such groups may be straight chain or branched. Aptly, lower alkyl groups include methyl, ethyl, n-propyl, iso-propyl and n-butyl groups.

Most suitably $R^1$ and $R^2$ both represent the same kind of lower alkyl group or alternatively are linked.

Particularly suitable acyclic values for $R^1$ and $R^2$ are the methyl and ethyl groups, especially ethyl. Particularly suitable cyclic values when $R^1$ and $R^2$ are taken together are the 1,3-dioxa-cyclopenta-2,2-diyl ($R^1$, $R^2$ together are ethylene) and 1,3-dioxacyclohexa,2,2 diyl ($R^1$, $R^2$ are together trimethylene) diradicals especially 1,3-dioxacyclopenta-2,2-diyl.

Particularly suitable values for $R^3$ and $R^4$ are the ethyl and n-butyl groups, especially n-butyl. $R^3$ and $R^4$ are often the same.

A preferred group of compounds within those of the formula (II) is those of the formula (III):

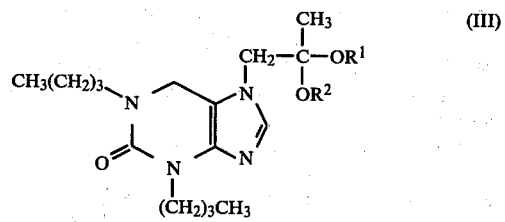

wherein $R^1$ and $R^2$ are as defined in formula (II).
Particularly suitable $R^1$ and $R^2$ are as so described under formula (II). Especially suitably $R^1$ and $R^2$ are each individually ethyl or taken together ethylene.

A second preferred group of compounds within those of the formula (II) is those of the formula (IV):

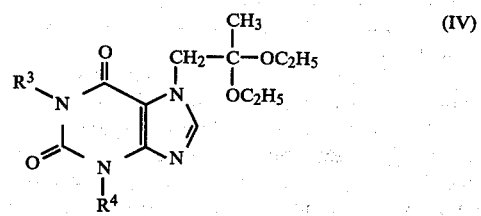

wherein $R^3$ and $R^4$ are as defined in formula (II).
Particularly suitable $R^3$ and $R^4$ are as so described under formula (II). Especially suitably $R^3$ and $R^4$ are each n-butyl.

A third preferred group of compounds within those of the formula (II) is those of the formula (V):

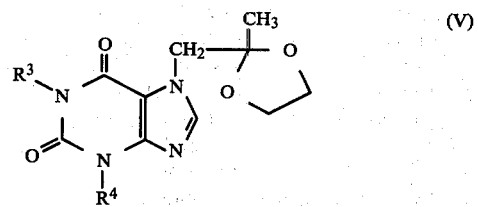

wherein $R^3$ and $R^4$ are as defined in formula (II).
Particularly suitable $R^3$ and $R^4$ are as so described under formula (II). Especially suitably $R^3$ and $R^4$ are each n-butyl or ethyl.

A group of compounds of the present invention is:
1,3-dibutylxanthin-7-ylpropan-2-one diethyl ketal,
1,3-dibutylxanthin-7-ylpropan-2-one dimethyl ketal,
1,3-diethylxanthin-7-ylpropan-2-one diethyl ketal,
2-methyl-2-[(1,3-dibutylxanthin-7-yl)methyl]-1,3-dioxalane,
2-methyl-2-[(1,3-diethylxanthin-7-yl)methyl]-1,3-dioxalane,
2-methyl-2-[(1-butyl-3-ethylxanthin-7-yl)methyl]-1,3-dioxalane, and
2-methyl-2-[(1,3-dibutylxanthin-7-yl)methyl]-1,3-dioxacyclohexane Preferred compounds are:
1,3-dibutylxanthin-7-ylpropan-2-one diethyl ketal and
2-methyl-2-[(1,3-dibutylxanthin-7-yl)methyl]-1,3-dioxalane,
1,3-dibutylxanthine-7-ylpropan-2-one dimethyl ketal,
1,3-diethylxanthine-7-ylpropan-2-one diethyl ketal.

The compounds of this invention may be used to treat vascular disorders such as intermittent claudication. Thus the present invention also provides a pharmaceutical composition which comprises a compound of the formula (II) and a pharmaceutically acceptable carrier.

Although the compositions of this invention may be in a form suitable for administration by injection, it is preferred that the compositions are adapted for oral administration since this allows for more convenient administration. The compositions of this invention are most suitably provided in unit dose forms, for example as a tablet or capsule. Such dosage forms may, for example, contain 5 to 500 mgs or more usually from 10 to 200 mgs, for example from 15 to 150 mgs. Thus advantageously the unit dose composition of this invention may contain 15, 20, 25, 50, 75, 100 or 150 mgs or the like of the active agent. Such unit dosage forms are normally administered from 1 to 4 times daily in such a way that the daily dose for a 70 kg adult will normally be in the range 40 to 1000 mgs and more usually from 50 to 900 mgs for example 60 to 800 mgs.

Particularly suitable unit dosage forms are tablets and capsules.

The compositions of this invention may be formulated in conventional manner. Thus oral dosage units may contain such conventional agents as fillers (diluents), lubricants, binders, disintegrants, colourants, flavourings, surface active agents, preservatives, buffering agents and the like. Suitable fillers for use include cellulose, manitol, lactose and other similar agents. Suitable disintegrants include starch, polyvinylpolypyrrolidone and starch derivatives such as sodium starch glycollate and the like. Suitable lubricants include stearic acid, magnesium stearate, magnesium lauryl sulphate and the like. Injectable compositions may consist essentially of a sterile, pyrogen free compound of this invention sealed into a vial optionally together with suspending and preserving agents. Such compositions may be made up for administration with sterile water or saline.

The compositions may be prepared by conventional methods of blending, filling, tabletting or the like.

The present invention also provides a process for the preparation of the compounds of this invention which process comprises the reaction of a salt of a 1,3-dilower alkylxanthine with a compound of the formula (VI):

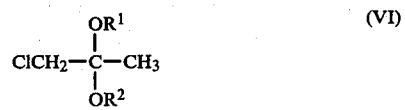

or the chemical equivalent thereof wherein $R^1$ and $R^2$ are as defined in relation to formula (II).

Suitable chemical equivalents of the compound of the formula (VI) include the corresponding bromo and iodo compounds and activated esters such as the methanesulphonate or p-toluenesulphonate.

The condensation reaction is generally effected in an organic solvent such as a lower alkanol or acetone.

The xanthine salt may be preformed or formed in situ, for example by sodium hydroxide, potassium hydroxide an alkali metal alkoxide or the like.

In a further and often more convenient process aspect this invention provides a process for the preparation of a compound of the formula (VI) which comprises ketalising the corresponding 1,3-di-lower alkyl-7-(2-oxopropyl) xanthine.

Such ketalisation may be carried out under conventional conditions. Thus for the preparation of cyclic ketals for example a water-free solvent such as benzene or xylene and a catalytic amount of a dehydrating acid such as p-toluenesulphonic acid may be used with a diol at an elevated temperature, for example at reflux temperature. Alternatively, for acyclic ketals, an orthoester may be used at ambient temperature in the presence of a catalyst such as Amberlyst 15 (see Patwardhan et al., Synthesis, 1974, page 348). In this form of the process a large excess of the orthoester may be used so that the orthoester also acts as solvent.

The desired product may be obtained by evaporating the reaction mixture after washing. The initially obtained product may be purified in conventional manner, for example by recrystallisation from petroleum ether.

The following Examples illustrate the preparation of compounds of the present invention:

EXAMPLE 1

1,3-Dibutylxanthin-7-ylpropan-2-one diethyl ketal (1)

1,3-Dibutyl-7-(2-oxopropyl)-xanthine (32 g), orthoformic acid triethyl ester (150 ml) and Amberlyst 15 (7 g) were stirred over night at room temperature. After addition of a further amount of Amberlyst 15 (72 g), the reaction mixture was stirred for a further 3 hours at room temperature. The Amberlyst 15 was then filtered off and washed with chloroform. The combined solutions were evaporated to dryness in vacuo and the residue purified by column chromatography to yield 1,3-dibutylxanthin-7-yl(propan-2-one)diethyl ketal (15.2 g).

Elemental Analysis

|   | Calculated | Found |
|---|---|---|
| C | 60.89 | 61.10 |
| H | 8.69  | 8.25  |
| N | 14.20 | 14.15 |
| O | 16.22 | 16.41 |

The structure was confirmed by NMR spectroscopy.

Using analogous procedures the following were prepared:

1,3-dibutylxanthin-7-ylpropan-2-one dimethyl ketal (2)

Elemental analysis

|   | Calculated | Found |
|---|---|---|
| C | 59.00 | 58.92 |
| H | 8.25  | 8.23  |
| N | 15.29 | 15.26 |
| O | 17.46 | 17.42 |

1,3-diethylxanthinyl-7-ylpropan-2-one diethyl ketal (3)

Elemental analysis

|   | Calculated | Found |
|---|---|---|
| C | 56.78 | 56.72 |
| H | 7.44  | 7.69  |
| N | 16.55 | 16.65 |
| O | 18.91 | 18.85 |

EXAMPLE 2

2-Methyl-2-[(1,3-di-n-butylxanthin-7-yl)methyl]-1,3-dioxalane (4)

1,3-Dibutyl-7-(2-oxopropyl)-xanthine (16 g), ethylene glycol (6.8 ml), xylene (80 ml) and p-toluenesulphonic acid (0.0005 g) were treated for several days under reflux. The reaction water was removed by a water separator. After cooling at room temperature the unreacted ethyleneglycol was separated from the xylene phase. Petrolether (40/80°) was then added and the resulting precipitate of unreacted 1,3-dibutyl-7-(2-oxopropyl)-xanthine removed by suction. From the remaining xylene solution the xylene was removed under reduced pressure. The oily residue crystallized over a period of several days. This crude 2-methyl-2-[(1,3-di-n-butylxanthin-7-yl)-methyl]-1,3 dioxalane was filtered off by suction and recrystallized from petrolether to yield 4.4 g of solid, m.pt. 73° C.

Elemental Analysis

|   | Calculated | Found |
|---|---|---|
| C | 59.32 | 59.83 |
| H | 7.74 | 7.54 |
| N | 15.38 | 15.19 |
| O | 17.56 | 17.65 |

The structure was confirmed by NMR spectroscopy.

Using analogous procedures the following were prepared:

2-methyl-2-[(1,3-diethylxanthin-7-yl)methyl]-1,3-dioxalane (5)

Elemental analysis

|   | Calculated | Found |
|---|---|---|
| C | 54.53 | 54.90 |
| H | 6.53 | 6.47 |
| N | 18.1 | 17.82 |
| O | 20.75 | 20.86 |

2-Methyl-2-[(1-n-butyl-3-ethyl-xanthin-7-yl)-methyl]-1,3-dioxalane (6)

M.pt. 68° C.

Elemental Analysis

|   | Calculated | Found |
|---|---|---|
| C | 57.13 | 56.98 |
| H | 7.19 | 7.16 |
| N | 16.66 | 17.14 |
| O | 19.02 | 18.80 |

2-methyl-2-[(1,3-dibutylxanthin-7-yl) methyl]-1,3-dioxacyclohexane (7)

Elemental analysis

|   | Calculated | Found |
|---|---|---|
| C | 60.30 | 60.13 |
| H | 7.99 | 7.87 |
| N | 14.80 | 14.94 |
| O | 16.91 | 16.87 |

EXAMPLE 3

Composition

2-Methyl-2-[(1,3-di-n-butylxanthin-7-yl)-methyl]-1,3-dioxalane, magnesium stearate and microcrylstalline cellulose may be blended together, passed through a 40 mesh sieve (U.K.) and tabletted on a conventional rotatory machine to produce a batch of 5000 tablets of the following composition:

| Active agent | 50 mg |
|---|---|
| Magnesium stearate | 0.2 mg |
| Microcrystalline cellulose | 149.8 mg |

ILLUSTRATION OF PHARMACOLOGICAL EFFECTIVENESS

Methodology

Cats of either sex were anaesthetized by i.p. injection of urethane/chloralose (120/60 mg/kg). The intraduodenal (i.d.) administration of compounds was conducted by means of a plastic catheter which was inserted into the duodenum following midline incision at the abdominal cavity.

(i) $pO_2$-measurements

Measurement of muscle surface $pO_2$. The skin above the measuring site (3–4 mm in diameter) was removed and one multiwire-surface electrode (Eschweiler, Kiel) was placed on the gastrocnemius muscle of each hindlimb. The femoral artery in one hindlimb was ligated in order to induce ischaemia. Muscle temperature was controlled by means of a thermocouple (Ellab, Copenhagen). The electrode current was measured every 6 to 8 s and collected for periods of 4 min (Hewlett-Packard programmable data logger system 3051 A). After each period, mean value and standard deviation was calculated.

(ii) Skeletal muscle contractility

After dissection of the skin of the calf muscles, the sciatic nerve was cut about 3 cm proximal to the knee. The tendon of the calf muscles was cut and connected with an isometric force transducer (SWEMA, SG 3). In order to maintain constant differences and a resting tension of 100 p in cats and 25 p in rats, the hindlimb was fixed at the tibia by means of a clamp. Direct stimulation of the muscles consisted of square wave pulses of 4 msec duration at a frequency of 2 Hz and at a voltage 50 V in cats. In order to keep the muscles wet and at a normal temperature, the muscles were continuously superfused with 0.9% w/v NaCl solution (38° C.). Femoral blood flow was restricted by a graded occlusion of the artery leading to a reduction of contractility by ca. 30%. After having reached a constant level of the contraction force, the appropriate vehicle (NaCl or Methocel) was injected, followed by the test substance.

RESULTS (i) $pO_2$ measurements

| Compound | dosage (mg/kg) i.d.* | n | hypoxic tissue $C_s$ | hypoxic tissue $\overline{\Delta pO_2}$ (Torr) | hypoxic tissue E (Torr) | normoxic tissue $C_s$ | normoxic tissue $\overline{\Delta pO_2}$ (Torr) | normoxic tissue E (Torr) |
|---|---|---|---|---|---|---|---|---|
| 1 | 0.8 | 4 | 1 | 12.8 | 12.8 | 1 | 14.3 | 14.3 |
| 3 | 32.0 | 2 | 1 | 13.5 | 13.5 | 0.5 | 22.3 | 11.2 |
| 2 | 2.0 | 2 | 1 | 7.8 | 7.8 | 1 | 13.7 | 13.7 |
| 4 | 0.8 | 3 | 1 | 6.4 | 6.4 | 1 | 7.7 | 7.7 |
| 6 | 12.5 | 3 | 1 | 13.8 | 13.8 | 1 | 29.6 | 29.6 |

(ii) Sketal muscle contractility under ischaemic conditions

| substance | dosage (mg/kg) i.d.* | n | increase of contractility (% of initial values) |
|---|---|---|---|
| 1 | 0.8 | 4 | +17.2 |
| 3 | 32.0 | 2 | +35.2, +45.0 |
| 2 | 2.0 | 4 | +26.7 |
| 6 | 12.5 | 2 | +28.6, +25.0 | control values (Methocel°): ±0 n = number of animals
$C_s$ = significance coefficient = number of measuring sites with significant $pO_2$ increase per total number of measuring sites
$\overline{\Delta pO_2}$ = mean $pO_2$ increase in experiments with significant $pO_2$ increase (Torr)
E = efficiency-index = $C_s \times \overline{\Delta pO_2}$ (Torr)
Control values: E = between 0.1 and 1.2 Torr
i.d.* = intraduodenal administration of a suspension in Methocel°

TOXICITY

No toxic effects were observed at the above test dosages.

I claim:

1. A compound having the formula (III):

wherein $R^1$ and $R^2$ are are lower alkyl or taken together are $C_2$-$C_4$ alkylene.

2. A compound having the formula (IV):

wherein $R^3$ and $R^4$ are ethyl or butyl.

3. 1,3-dibutylxanthin-7-ylpropan-2-one diethyl ketal.

4. A compound having the formula (V):

wherein $R^3$ and $R^4$ are the same or different lower alkyl.

5. 2-methyl-2-[1,3-dibutylxanthin-7-yl)methyl]-1,3-dioxalane.

6. A compound of the formula (II):

wherein $R^1$ and $R^2$ taken together are ethylene, trimethylene or tetramethylene, and
$R_3$ and $R_4$ are the same or different and are each lower alkyl.

7. A method of treating vascular disorders in humans and animals which comprises administering to the sufferer an effective amount of a compound of the formula (II):

each of $R^1$ and $R^2$ is lower alkyl or $R^1$ and $R^2$ taken together are ethylene, trimethylene or tetramethylene and $R^3$ and $R^4$ are the same or different lower alkyl.

8. A pharmaceutical composition useful for treating vascular disorders, which comprises an amount of a compound according to claim 2, sufficient to improve vascular flow in combination with a pharmaceutically acceptable carrier therefor.

9. A pharmaceutical composition useful for treating vascular disorders, which comprises an amount of a compound according to claim 3, sufficient to improve vascular flow in combination with a pharmaceutically acceptable carrier therefor.

10. A pharmaceutical composition useful for treating vascular disorders, which comprises an amount of a compound according to claim 4, sufficient to improve vascular flow in combination with a pharmaceutically acceptable carrier therefor.

11. A pharmaceutical composition useful for treating vascular disorders which comprises an amount of a compound according to claim 5, sufficient to improve vascular flow in combination with a pharmaceutically acceptable carrier therefor.

12. A pharmaceutical composition useful for treating vascular disorders which comprises an amount of a compound according to claim 6, sufficient to improve vascular flow in combination with a pharmaceutically acceptable carrier therefor.

13. A pharmaceutical composition useful for treating vascular disorders which comprises an amount of a compound according to claim 9, sufficient to improve vascular flow in combination with a pharmaceutically acceptable carrier therefor.

* * * * *

UNITED STATES PATENT AND TRADEMARK OFFICE
CERTIFICATE OF CORRECTION

PATENT NO. : 4,451,449
DATED : May 29, 1984
INVENTOR(S) : JOACHIM EWALD GORING

It is certified that error appears in the above-identified patent and that said Letters Patent are hereby corrected as shown below:

On the title page,

In item [73] the correct name of the Assignee should read

-- Johanna A. Wuelfing --.

Signed and Sealed this

Twelfth Day of March 1985

[SEAL]

Attest:

DONALD J. QUIGG

*Attesting Officer*   *Acting Commissioner of Patents and Trademarks*

UNITED STATES PATENT AND TRADEMARK OFFICE
CERTIFICATE OF CORRECTION

PATENT NO. : 4,451,449
DATED : May 29, 1984
INVENTOR(S) : JOACHIM EWALD GORING

It is certified that error appears in the above-identified patent and that said Letters Patent is hereby corrected as shown below:

On the title page,
In item [73] the correct name of the Assignee should read
-- JOHANN A. WUELFING --.

This certificate supersedes certificate of correction issued March 12, 1985.

Signed and Sealed this

Twenty-eighth Day of May 1985

[SEAL]

Attest:

DONALD J. QUIGG

Attesting Officer

Acting Commissioner of Patents and Trademarks